(12) United States Patent
Ahn et al.

(10) Patent No.: US 11,034,802 B2
(45) Date of Patent: *Jun. 15, 2021

(54) SUPERABSORBENT POLYMER AND METHOD FOR PREPARING THE SAME

(71) Applicant: LG Chem, Ltd., Seoul (KR)

(72) Inventors: Taebin Ahn, Daejeon (KR); Dong Hyun Kim, Daejeon (KR); Chang Hun Han, Daejeon (KR)

(73) Assignee: LG Chem, Ltd.

( * ) Notice: Subject to any disclaimer, the term of this patent is extended or adjusted under 35 U.S.C. 154(b) by 110 days.

This patent is subject to a terminal disclaimer.

(21) Appl. No.: 16/341,292

(22) PCT Filed: Aug. 7, 2018

(86) PCT No.: PCT/KR2018/008983
§ 371 (c)(1),
(2) Date: Apr. 11, 2019

(87) PCT Pub. No.: WO2019/117418
PCT Pub. Date: Jun. 20, 2019

(65) Prior Publication Data
US 2020/0216623 A1 Jul. 9, 2020

(30) Foreign Application Priority Data
Dec. 14, 2017 (KR) .................. 10-2017-0172277

(51) Int. Cl.
| | | |
|---|---|---|
| C08J 3/12 | (2006.01) | |
| A61L 15/24 | (2006.01) | |
| A61L 15/60 | (2006.01) | |
| C08J 3/24 | (2006.01) | |
| C08K 3/22 | (2006.01) | |
| C08K 3/36 | (2006.01) | |
| C08K 9/06 | (2006.01) | |

(52) U.S. Cl.
CPC ............ *C08J 3/124* (2013.01); *A61L 15/24* (2013.01); *A61L 15/60* (2013.01); *C08J 3/245* (2013.01); *C08K 3/22* (2013.01); *C08K 3/36* (2013.01); *C08K 9/06* (2013.01); *C08J 2333/02* (2013.01); *C08K 2003/2227* (2013.01)

(58) Field of Classification Search
CPC ...................................................... A61L 15/60
See application file for complete search history.

(56) References Cited

U.S. PATENT DOCUMENTS

| | | | |
|---|---|---|---|
| 4,883,478 A | 11/1989 | Lerailler et al. | |
| 10,023,703 B2* | 7/2018 | Lee et al. | |
| 10,773,237 B2* | 9/2020 | Yoon | C08K 9/02 |
| 2010/0047445 A1 | 2/2010 | Barthel et al. | |
| 2011/0301560 A1 | 12/2011 | Fujimura et al. | |
| 2013/0130895 A1 | 5/2013 | Herfert et al. | |
| 2015/0259522 A1 | 9/2015 | Lee et al. | |
| 2015/0307667 A1 | 10/2015 | Wada et al. | |
| 2016/0235882 A1 | 8/2016 | Noh et al. | |
| 2017/0036191 A1 | 2/2017 | Yang et al. | |
| 2017/0326528 A1 | 11/2017 | Park et al. | |
| 2018/0147557 A1 | 5/2018 | Hwang et al. | |
| 2018/0243464 A1 | 8/2018 | Hwang et al. | |
| 2018/0297012 A1 | 10/2018 | Kim et al. | |
| 2018/0304232 A1 | 10/2018 | Nam et al. | |

FOREIGN PATENT DOCUMENTS

| | | |
|---|---|---|
| EP | 3031857 A1 | 6/2016 |
| EP | 3101038 A1 | 12/2016 |
| EP | 3112022 A1 | 1/2017 |
| EP | 3243859 A1 | 11/2017 |
| EP | 3336133 A1 | 6/2018 |
| JP | 2000093792 A | 4/2000 |
| JP | 2010521578 A | 6/2010 |
| KR | 20110114535 A | 10/2011 |
| KR | 20150069320 A | 6/2015 |
| KR | 101559081 B1 | 10/2015 |
| KR | 101645684 B1 | 8/2016 |
| KR | 20160091242 A | 8/2016 |
| KR | 20160144611 A | 12/2016 |
| KR | 20170096805 A | 8/2017 |
| KR | 20170098196 A | 8/2017 |
| KR | 20170111295 A | 10/2017 |
| KR | 20170112877 A | 10/2017 |
| WO | 8703208 A1 | 6/1987 |
| WO | 2006109844 A1 | 10/2006 |
| WO | 2006109882 A1 | 10/2006 |
| WO | 2013076031 A1 | 5/2013 |
| WO | 2014088012 A1 | 6/2014 |

(Continued)

OTHER PUBLICATIONS

Third Party Observation for PCT/KR2018/008983 submitted Feb. 5, 2020, 10 pages.
Extended European Search Report including Written Opinion for Application No. EP18863809.2 dated Dec. 9, 2019.
International Search Report for PCT/KR2018/008983 dated Jan. 2, 2019.
Schwalm, Reinhold, "UV Coatings: Basics, Recent Developments and New Applications." Elsevier Science, Dec. 21, 2006, p. 115.
Odian, George, "Principles of Polymerization." Second Edition, 1981, John Wiley & Sons, Inc., p. 203.

*Primary Examiner* — Michael F Pepitone
(74) *Attorney, Agent, or Firm* — Lerner, David, Littenberg, Krumholz & Mentlik, LLP

(57) ABSTRACT

The superabsorbent polymer has absorption under pressure/ under no pressure, permeability, and absorption speed that are suitable for the application in thin hygienic goods, and simultaneously, inhibits the generation of dust in the preparation process of hygienic goods and does not exhibit blocking in the preparation process of the superabsorbent polymer.

18 Claims, No Drawings

(56) References Cited

FOREIGN PATENT DOCUMENTS

WO  WO-2015190878 A1 * 12/2015 ............ C08F 265/06
WO     2017142230 A1    8/2017

* cited by examiner

SUPERABSORBENT POLYMER AND METHOD FOR PREPARING THE SAME

CROSS-REFERENCE TO RELATED APPLICATIONS

The present application is a national phase entry under 35 U.S.C. § 371 of International Application No. PCT/KR2018/008983 filed on Aug. 7, 2018, which claims priority from Korean Patent Application No. 10-2017-0172277 filed on Dec. 14, 2017, all of which are incorporated herein by reference.

TECHNICAL FIELD

The present invention relates to a superabsorbent polymer having excellent absorption performance, and a method for preparing the same.

BACKGROUND OF ART

A superabsorbent polymer (SAP) is a synthetic polymer material that can absorb moisture at 500 to 1000 times its own weight, and is also called a super absorption material (SAM), an absorbent gel material (AGM), etc. according to developing companies. The superabsorbent polymer began to be commercialized for sanitary items, and currently, it is being widely used for hygienic goods such as disposable diapers and so on, a water-holding material for soil, a water stop material for civil engineering and architecture, sheets for raising seedling, freshness preservatives in the field of food circulation, fomentation material, etc.

In most cases, such a superabsorbent polymer is being widely used in the field of hygienic goods such as diapers sanitary pads, etc. In the hygienic goods, the superabsorbent polymer is generally included while being spread in pulp. However, recently, there have been continued attempts to provide hygienic goods such as diapers with a thinner thickness. With the increasing demand for thin hygienic goods, the rate of liquid absorption of the absorbent polymer in the hygienic goods tends to increase. For this, the absorbent polymer is required to simultaneously have the performance of the pulp. Thus, it should have high permeability and absorption speed as well as a high absorption rate.

In order to improve absorption speed, in general, a blowing agent is used or a hydrogel is ground with high energy, but in this case, a porous structure is formed on the surface and inside, and thus it is easily broken by an external force such that dust is generated in the preparation processes of superabsorbent polymer and hygienic goods, thus rendering the operation difficult, and inducing blocking during the process.

In order to solve the dust generation and blocking during the process, in the prior art, the strength of a reassembled body was improved (Korean Registered Patent No. 10-1559081), or the amount of dust generation was reduced by increasing moisture content (International Application No. PCT/JP2013/082503), but according to these methods, it is insufficient to secure adequate permeability dependent absorption under pressure (PDAUP) and absorption speed (vortex) of the recently required levels. Further, a method of mixing inorganic particles has been suggested so as to only solve the blocking problem (U.S. Patent Publication Laid-Open No. 2013/0130895), but it has problems in that the inorganic particles are desorbed from the surface of the superabsorbent polymer to increase dust, thus deteriorating the properties of the absorbent polymer.

DETAILED DESCRIPTION OF THE INVENTION

Technical Problem

It is an object of the present invention to provide a superabsorbent polymer that has absorption under pressure/under no pressure, permeability, and absorption speed that are suitable for application in thin hygienic goods, and that simultaneously inhibits the generation of dust in the preparation process of hygienic goods and does not exhibit blocking in the preparation process of the absorbent polymer.

Technical Solution

In order to solve the problem, the present invention provides a superabsorbent polymer including
base polymer powder including a first crosslinked polymer of water soluble ethylenically unsaturated monomers having acid groups of which at least a part are neutralized; and
a surface crosslink layer formed on the base polymer powder, including a second crosslinked polymer obtained by additional crosslinking of the first crosslinked polymer by a surface crosslinking agent,
wherein centrifuge retention capacity (CRC) is 26 g/g or more,
absorption under pressure of 0.7 psi (0.7 AUP) is 18 g/g or more,
permeability dependent absorption under pressure (PDAUP) is 15 g/g or more,
absorption speed measured according to a vortex measuring method is 80 seconds or less, and
anticaking efficiency is 30% or more.

The present invention provides a superabsorbent polymer that has absorption under pressure/under no pressure, permeability, and absorption speed that are suitable for the application in thin hygienic goods, and simultaneously, inhibits the generation of dust in the preparation process of hygienic goods and does not exhibit blocking in the preparation process of the absorbent polymer. Further, it has been confirmed that if hydrophilic inorganic particles and hydrophobic inorganic particles are used during the preparation process of a superabsorbent polymer, particularly during surface crosslinking and post treatment thereof as explained below, the above-described effects can be achieved.

Hereinafter, the present invention will be explained in detail.

Superabsorbent Polymer

The water soluble ethylenically unsaturated monomers making up the first crosslinked polymer may be any monomers commonly used for the preparation of a superabsorbent polymer. As non-limiting examples, the water soluble ethylenically unsaturated monomers may be compounds represented by the following Chemical Formula 1.

$R_1$—COOM$^1$     [Chemical Formula 1]

In Chemical Formula 1,
$R_1$ is a C2-5 alkyl group including an unsaturated bond,
$M^1$ is a hydrogen atom, a monovalent or divalent metal, an ammonium group, or an organic amine salt.

Preferably, the monomers may be one or more kinds selected from the group consisting of acrylic acid, methacrylic acid, and a monovalent metal salt, a divalent metal salt, an ammonium salt, and an organic amine salt thereof. As such, if acrylic acid or a salt there of is used as the water soluble ethylenically unsaturated monomers, a superabsorbent polymer with an improved absorption property may be obtained. In addition, as the monomers, maleic anhydride, fumaric acid, crotonic acid, itaconic acid, 2-acryloyl ethane sulfonic acid, 2-methacryloyl ethane sulfonic acid, 2-(meth) acryloyl propane sulfonic acid, or 2-(meth)acrylamide-2-methylpropane sulfonic acid, (meth)acrylamide, N-substituted (meth)acrylate, 2-hydroxyethyl (meth)acrylate, 2-hydroxypropyl (meth)acrylate, methoxypolyethylene glycol, (meth)acrylate, polyethylene glycol (meth)acrylate, (N,N)-dimethylaminoethyl (meth)acrylate, (N,N)-dimethylaminopropyl (meth)acrylamide, etc. may be used.

Here, the water soluble ethylenically unsaturated monomers may have acid groups, and at least a part of the acid groups may be neutralized. Preferably, monomers that are partially neutralized by an alkali material such as sodium hydroxide, potassium hydroxide, ammonium hydroxide, etc. may be used.

Here, the degree of neutralization of the monomers may be 40 to 95 mol %, 40 to 90 mol %, or 45 to 85 mol %. The degree of neutralization may vary according to the final properties, but if the degree of neutralization is too high, neutralized monomers may be precipitated, rendering smooth progression of polymerization difficult, and to the contrary, if the degree of neutralization is too low, absorption force of the polymer may be significantly lowered, and it may exhibit a rubber-like property, which is difficult to handle.

Preferably, the surface crosslink layer includes hydrophilic inorganic particles, and hydrophobic inorganic particles are included on the surface of the surface crosslink layer. That is, the surface crosslink layer includes a second crosslinked polymer obtained by additional crosslinking of the surface of the base polymer powders by a surface crosslinking agent and hydrophilic inorganic particles, and the surface crosslinking agent and the surface crosslinking method will be explained later. Further, hydrophobic inorganic particles are included on the surface crosslink layer.

As the hydrophilic inorganic particles, silica particles or metal oxide particles may be used. As the metal oxide particles, aluminum oxide particles or titanium oxide particles may be used. The hydrophilic inorganic particles are those that are not chemically treated on the surface of silica particles or metal oxide particles, and the surface exhibits hydrophilicity.

The hydrophobic inorganic particles are inorganic particles exhibiting hydrophobicity by treating the surface of silica particles or metal oxide particles with a compound having a hydrophobic group, specifically, a siloxane, silane, or silazane compound. Preferably, the hydrophobic inorganic particles are surface-treated with hexamethyldisilazane, polydimethylsiloxane, or dimethyldichlorosilane. That is, the hydrophobic inorganic particles mean those obtained by treating the surface of the hydrophilic inorganic particles with a compound having a hydrophobic group.

The hydrophilic inorganic particles or hydrophobic inorganic particles may have a BET specific surface area of 5 to 500 $m^2/g$, 25 to 450 $m^2/g$, or 50 to 400 $m^2/g$, respectively.

Meanwhile, the superabsorbent polymer according to the present invention may have a centrifuge retention capacity (CRC) to a saline solution (0.9 wt % sodium chloride aqueous solution) for 30 minutes of 26 g/g or more. The centrifuge retention capacity means a capacity for retaining moisture absorbed by the superabsorbent polymer. A specific measuring method thereof will be described in the examples below.

Preferably, the centrifuge retention capacity is 27 g/g or more, or 28 g/g or more. The higher the centrifuge retention capacity value, the better it is, and the upper limit is not theoretically limited, but for example, it is 45 g/g or less, or 44 g/g or less.

The superabsorbent polymer according to the present invention may have absorption under pressure of 0.7 psi (0.7 AUP), of 18 g/g or more. The 0.7 AUP means the amount of brine absorbed for 1 hour under pressure of 0.7 psi, and it means the total amount of water which the superabsorbent polymer can absorb. A specific measuring method thereof will be described in the examples below.

Preferably, the 0.7 AUP is 19 g/g or more, or 20 g/g or more. The higher the 0.7AUP value, the better it is, and the upper limit is not theoretically limited, but for example, it is 29 g/g or less, or 28 g/g or less.

The superabsorbent polymer according to the present invention may have permeability dependent absorption under pressure (PDAUP) of 15 g/g or more. Although the PDAUP is similar to AUP, it means the amount of brine absorbed for 1 hour while increasing the amount of superabsorbent polymer, and evaluates AUP considering permeability. A specific measuring method thereof will be described in the examples below.

Preferably, the PDAUP is 15 g/g or more, or 16 g/g or more. The higher the PDAUP value, the better it is, and the upper limit is not theoretically limited, but for example, it is 24 g/g or less, or 23 g/g or less.

The superabsorbent polymer according to the present invention may have an absorption speed, measured according to a vortex measuring method, of 80 seconds or less. The absorption speed means a time when the vortex of liquid disappears by rapid absorption, when the superabsorbent polymer is added to a saline solution and stirred, and it means the rapid absorption capacity of the superabsorbent polymer. A specific measuring method thereof will be described in the examples below.

Preferably, the absorption speed, measured according to vortex measuring method, is 80 seconds or less, or 75 seconds or less. The smaller the value of the absorption speed measured according to a vortex measuring method, the better it is, and the lower limit is theoretically 0 seconds, but for example, it is 25 seconds or more, or 30 seconds or more.

The superabsorbent polymer according to the present invention may have anticaking efficiency of 30% or more. The anticaking efficiency evaluates the degree of hardening when the superabsorbent polymer is stored, and is measured according to the following Mathematical Formula 1. A specific measuring method thereof will be described in the examples below.

anticaking efficiency (%)= $(W_1)/(W_1+W_2) \times 100$     [Mathematical Formula 1]

In Mathematical Formula 1, $W_1$ is the weight of the superabsorbent polymer dropped on the bottom, after 2 g of the superabsorbent polymer is uniformly sprayed onto a glass Petri dish with an inner diameter of 95 mm, and then moisturized in a constant temperature and humidity chamber at a temperature of 40° C. and relative humidity of 80% for 10 minutes, taken out, and turned over for 5 minutes, and $W_2$ is the weight of the superabsorbent polymer remaining in the glass Petri dish.

Preferably, the anticaking efficiency is 35% or more, or 40% or more. The higher the anticaking efficiency value, the better it is, and the theoretical upper limit is 100%, but for example, it is 99% or less, or 98% or less.

Preferably, the superabsorbent polymer according to the present invention has an average particle diameter of 300 to 600 μm, and 10 to 90 wt % of the superabsorbent polymer has a particle diameter of 300 to 600 μm. More preferably, 10 wt % or more of the superabsorbent polymer has a particle diameter of 300 μm or less.

The superabsorbent polymer according to the present invention may have a small dust generation degree as described below in the examples, thus inhibiting dust generation in the preparation process of hygienic goods.

A method for Preparing Superabsorbent Polymer

The present invention provides a method for preparing the above-explained superabsorbent polymer including the steps of:
conducting crosslinking polymerization of water soluble ethylenically unsaturated monomers having acid groups of which at least a part are neutralized, in the presence of an internal crosslinking agent, to form a hydrogel polymer including a first crosslinked polymer (step 1);
coarsely grinding the hydrogel polymer, and drying and grinding to prepare a base polymer powder (step 2);
conducting surface crosslinking of the base polymer powder by heat treatment, in the presence of a surface crosslinking solution including hydrophilic inorganic particles, to prepare superabsorbent polymer particles (step 3); and
coating hydrophobic inorganic particles on the superabsorbent polymer particles (step 4).

Hereinafter, the preparation method will be explained in detail according to each step.

(Step 1)

The step 1 is a step of forming a hydrogel polymer, wherein the crosslinking polymerization of a monomer composition including water soluble ethylenically unsaturated monomers having acid groups of which at least a part are neutralized, is conducted in the presence of an internal crosslinking agent.

Here, the water soluble ethylenically unsaturated monomers are as explained above. The concentration of the water soluble ethylenically unsaturated monomers in the monomer composition may be appropriately controlled considering polymerization time, reaction condition, etc., and preferably, it may be 20 to 90 wt %, or 40 to 65 wt %. Such a concentration range may be advantageous for controlling the grinding efficiency during grinding of a polymer described below, while obviating a need to remove non-reacted monomers after polymerization using a gel effect appearing in the polymerization reaction of the aqueous solution of a high concentration. However, if the concentration of the monomers is too low, the yield of the superabsorbent polymer may decrease. To the contrary, if the concentration of the monomers is too high, process problems may occur such as precipitation of a part of the monomers or a decrease in the grinding efficiency during grinding of the polymerized hydrogel polymer, and the properties of the superabsorbent polymer may be deteriorated.

As the internal crosslinking agent, any compounds can be used as long as they enable the introduction of crosslinking during the polymerization of the water soluble ethylenically unsaturated monomers. As non-limiting examples of the internal crosslinking agent, a multifunctional crosslinking agent such as polyethylene glycol diacrylate, N,N'-methylenebisacrylamide, trimethylolpropane tri(meth)acrylate, ethylene glycol di(meth)acrylate, polyethylene glycol (meth)acrylate, propylene glycol di(meth)acrylate, polypropylene glycol (meth)acrylate, butanediol di(meth)acrylate, butylene glycol di(meth)acrylate, diethylene glycol di(meth) acrylate, hexanediol di(meth)acrylate, triethylene glycol di(meth)acrylate, tripropylene glycol di(meth)acrylate, tetraethylene glycol di(meth)acrylate, dipentaerythritol pentaacrylate, glycerin tri(meth)acrylate, pentaerythritol tetraacrylate, triarylamine, allyl(meth)acrylate, propane diol, ethylene glycol diglycidyl ether, propylene glycol, glycerin, or ethylene carbonate may be used alone or in combinations, but are not limited thereto.

Such an internal crosslinking agent may be added at a concentration of about 0.001 to 1 wt %, based on the monomer composition. That is, if the concentration of the internal crosslinking agent is too low, the absorption speed of the polymer may decrease, and gel strength may become weak. To the contrary, if the concentration of the internal crosslinking agent is too high, the absorption force of the polymer may decrease, and thus it may not be preferable as an absorbent.

Further, in the step 1, a polymerization initiator commonly used in the preparation of a superabsorbent polymer may be included. As non-limiting examples of the polymerization initiator, a thermal polymerization initiator or a photopolymerization initiator may be used according to the polymerization method, and particularly, a thermal polymerization initiator may be used. However, even in the case of photopolymerization, since a certain amount of heat is generated by UV irradiation, etc., and heat is generated to some degree according to the progression of an exothermic polymerization reaction, a thermal polymerization initiator may be additionally included.

As the thermal polymerization initiator, at least one selected from the group consisting of a persulfate initiator, an azo initiator, hydrogen peroxide, and ascorbic acid may be used. Specific examples of the persulfate initiator may include sodium persulfate ($Na_2S_2O_8$), potassium persulfate ($K_2S_2O_8$), ammonium persulfate (($NH_4)_2S_2O_8$), etc., and specific examples of the azo initiator may include 2,2-azobis (2-amidinopropane)dihydrochloride, 2,2-azobis-(N,N-dimethylene)isobutyramidinedihydrochloride, 2-(carbamoylazo)isobutyronitril, 2,2-azobis[2-(2-imidazolin-2-yl) propane]dihydrochloride, 4,4-azobis-(4-cyanovalericacid), etc. More various thermal initiators are described in "Principle of Polymerization (Odian, 1981)", Published by Wiley, page 203, and are not limited to the above-described examples.

As the photopolymerization initiator, one or more selected from the group consisting of benzoin ether, dialkyl acetophenone, hydroxyl alkylketone, phenyl glyoxylate, benzyl dimethyl Ketal, acyl phosphine, and α-aminoketone may be used. Specific examples of the acyl phosphine may include commercially available Lucirin TPO, i.e., 2,4,6-trimethyl-benzoyl-trimethyl phosphine oxide. More various photopolymerization initiators are described in Reinhold Schwalm, "UV Coatings: Basics, Recent Developments and New Application (Elsevier 2007)", page 115, and are not limited to the above-described examples.

Such a polymerization initiator may be included at a concentration of about 0.001 to 1 part by weight, based on the monomer composition. That is, if the concentration of the polymerization initiator is too low, polymerization speed may become slow, and remaining monomers may be extracted in a large quantity in the final product. To the contrary, if the concentration of the polymerization initiator is higher than the above range, the polymer chain making up a network may be shortened, and thus the properties of the polymer may be deteriorated such as an increase in water soluble content and a decrease in absorption under pressure.

In addition, the monomer composition may further include a blowing agent, a surfactant, a thickener, a plasticizer, a preservation stabilizer, an antioxidant, etc., as necessary.

The monomer composition may be prepared in the form of a solution in which raw materials including the above-explained monomers, etc. are dissolved in a solvent. Here, the solvent that can be used is not limited in terms of its construction as long as it can dissolve or disperse the above-explained components, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methylethylketone, acetone, methyl amyl ketone, cyclohexanone, cyclopentanone, diethylene glycol monomethyl ether, diethylene glycol ethyl ether, toluene, xylene, butyrolactone, carbitol, methyl cellosolve acetate, N,N-dimethylacetamide, etc. may be used alone or in combination.

The formation of the hydrogel polymer through the polymerization of the monomer composition may be conducted by a common polymerization method, and the process is not specifically limited. As non-limiting examples, the polymerization method is largely classified into thermal polymerization and photopolymerization according to an energy source, and commonly, thermal polymerization may be progressed in a reactor equipped with a stirring axis such as a kneader, and photopolymerization may be progressed in a reactor equipped with a movable conveyer belt.

For example, a hydrogel polymer may be obtained by introducing the monomer composition into a reactor equipped with a stirring axis such as a kneader, and supplying hot air thereto or heating the reactor, thus conducting thermal polymerization. The hydrogel polymer discharged from the outlet of the reactor may be obtained in the size of a few centimeters to a few millimeters according to the shape of the stirring axis equipped in the reactor. Specifically, the size of the obtained hydrogel polymer may vary according to the concentration of the introduced monomer mixture, the introduction speed, etc., and commonly, a hydrogel polymer having a (weight average) particle diameter of 2 to 50 mm may be obtained.

Further, when photopolymerization is progressed in a reactor equipped with a movable conveyer belt as explained above, a hydrogel polymer in the form of a sheet may be obtained. Here, the thickness of the polymer sheet may vary according to the concentration of the introduced monomer mixture and the introduction speed, and it is preferable that the thickness is controlled to 0.5 to 5 cm so as to uniformly polymerize the whole sheet and simultaneously secure production speed.

The moisture content of hydrogel polymer obtained by such a method may be about 40 to about 80 wt %. Throughout the specification, the "moisture content" is the content of moisture occupied based on the total weight of the hydrogel polymer, and it means a value obtained by subtracting the weight of the polymer of a dry state from the weight of the hydrogel polymer. Specifically, it is defined as a value calculated by measuring the weight loss according to moisture evaporation in the polymer while raising the temperature of the polymer through infrared heating to dry it. At this time, the drying condition is established such that the temperature is raised from room temperature to about 180° C. and then maintained it at 180° C., and the total drying time is 20 minutes including a temperature raising step of 5 minutes.

(Step 2)

The step 2 is a step of coarsely grinding the hydrogel polymer prepared in step 1, and drying and grinding it to form a base polymer powder.

First, the hydrogel polymer prepared in step 1 is coarsely ground to prepare a hydrogel polymer of a small particle size.

Here, grinders that can be used in the coarse grinding are not limited in terms of constructions, but specifically, one selected from the group consisting of a vertical pulverizer, a turbo cutter, a turbo grinder, a rotary cutter mill, a cutter mill, a disc mill, a shred crusher, a crusher, a chopper, and a disc cutter may be used, but is not limited thereto.

Through the coarse grinding step, the particle diameter of the hydrogel polymer may be controlled to about 2 to about 10 mm. Grinding to a particle diameter of less than 2 mm would not be technically easy due to the high moisture content of the hydrogel polymer, and may generate agglomeration between the ground particles. Meanwhile, if grinding to a particle diameter of greater than 10 mm, the effect of increasing the efficiency of the subsequent drying step may be insignificant.

Subsequently, the coarsely ground hydrogel polymer is dried. The drying temperature may be about 50° C. to about 250° C. If the drying temperature is less than about 50° C., a drying time may too long, and the properties of the finally prepared superabsorbent polymer may be deteriorated, while if the drying temperature is greater than about 250° C., only the surface of the hydrogel polymer may be dried, thus generating fine powder in the subsequent grinding process, and the properties of the finally prepared superabsorbent polymer may be deteriorated. More preferably, the drying may be progressed at a temperature of about 150 to 200° C., more preferably at 160 to 190° C. Meanwhile, the drying may be progressed for 20 minutes to 15 hours, considering the process efficiency, etc., but is not limited thereto.

Further, the drying method is not limited in terms of the construction as long as it can be commonly used as a drying process of a hydrogel polymer. Specifically, the drying step may be progressed by hot wind supply, infrared ray irradiation, ultrahigh frequency wave irradiation, UV irradiation, etc. The polymer dried by such a method may exhibit a moisture content of about 0.05 to about 10 wt %.

Subsequently, the dried polymer is ground.

The particle diameter of the polymer powder obtained after the grinding step may be 150 μm to 850 μm. As a grinder for grinding to such a particle diameter, specifically, a pin mill, a hammer mill, a screw mill, a roll mill, a disc mill, a jog mill, etc. may be used, but the grinder is not limited thereto.

After the grinding step, a step of sieving the polymer powder according to the particle diameter may be conducted so as to manage the properties of the finally productized superabsorbent polymer. Preferably, a polymer with a particle diameter of 150 to 850 μm may be sieved, and only polymer powders having such particle diameters may be subjected to surface crosslinking and productized. It is more preferable that 90% or more of the polymer powders may have a particle diameter of 150 to 850 μm.

(Step 3)

The step 3 is a step of crosslinking the surface of the base polymer prepared in step 2, wherein the base polymer powder is heat treated in the presence of a surface crosslinking solution including hydrophilic inorganic particles to form superabsorbent polymer particles.

Here, the kinds of the surface crosslinking agent included in the surface crosslinking solution are not specifically limited. As non-limiting examples, the surface crosslinking agent may be one or more compounds selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol, trimethylolpropane, pentaerythritol, sorbitol, calcium hydroxide, magnesium hydroxide, aluminum hydroxide, iron hydroxide, calcium chloride, magnesium chloride, aluminum chloride, and iron chloride.

Here, the content of the surface crosslinking agent may be appropriately controlled according to the kind thereof or reaction condition, etc., and preferably, it may be controlled to 0.001 to 5 parts by weight, based on 100 parts by weight of the base polymer. If the content of the surface crosslinking agent is too low, surface crosslinking may not be properly introduced, and thus the properties of the final superabsorbent polymer may be deteriorated. To the contrary, if the content of the surface crosslinking agent is too high, due to an excessive surface crosslinking reaction, absorption force of the superabsorbent polymer may be lowered.

Further, the surface crosslinking solution may include one or more solvents selected form the group consisting of water, methanol, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methylethyl ketone, acetone, methyl amyl ketone, cyclohexanone, cyclopentanone, diethylene glycol monomethyl ether, diethylene glycol ethyl ether, toluene, xylene, butyrolactone, carbitol, methyl cellosolve acetate, and N,N-dimethylacetamide. The solvent may be included in the content of 0.5 to 15 parts by weight, based on 100 parts by weight of the base polymer.

The surface crosslinking solution includes hydrophilic inorganic particles.

The hydrophilic inorganic particles are as explained above, and preferably, they are included in the content of 0.002 to 0.25 parts by weight, based on 100 parts by weight of the base polymer.

Meanwhile, in order to conduct the surface crosslinking, the surface crosslinking solution and base polymer may be put in a reactor and mixed, a surface crosslinking solution may be sprayed to the base polymer, or a base polymer and a surface crosslinking solution may be continuously fed to a continuously operated mixer and mixed.

Preferably, the surface crosslinking is conducted by raising the temperature of the base polymer powder to 180° C. for 10 to 50 minutes, and heat treating at a temperature above 180° C. for 10 to 50 minutes. That is, the temperature sections for the surface crosslinking are substantially controlled to 2 stages, thus inducing surface crosslinking together with the hydrophilic inorganic particles to improve the properties of the superabsorbent polymer. The second temperature section is maintained above 180° C., preferably at 180 to 200° C.

(Step 4)

The step 4 is a step of coating hydrophobic inorganic particles on the superabsorbent polymer particles prepared in the step 3.

The hydrophobic inorganic particles as explained above. It is preferable that the hydrophobic inorganic particles are used in the content of 0.001 to 0.15 parts by weight, based on 100 parts by weight of the superabsorbent polymer particles.

Advantageous Effects

As explained above, the superabsorbent polymer according to the present invention has absorption under pressure/under no pressure, permeability, and absorption speed that are suitable for the application in thin hygienic goods, and simultaneously, inhibits the generation of dust in the preparation process of hygienic goods and does not exhibit blocking in the preparation process of the absorbent polymer.

DETAILED DESCRIPTION OF THE EMBODIMENTS

Hereinafter, preferable examples will be presented for better understanding of the present invention. However, these examples are presented only as illustrations of the invention, and the scope of the right of the invention is not limited thereby.

EXAMPLE 1

(Step 1)

100 parts by weight of acrylic acid was mixed with 0.2 parts by weight of polyethylene glycol diacrylate (weight average molecular weight: ~500 g/mol) and 0.1 parts by weight of ethoxylated trimethylol propane triacrylate (weight average molecular weight: ~700 g/mol) as internal crosslinking agents, and 0.01 parts by weight of IRGACURE 819 as a photoinitiator to prepare a monomer solution. Subsequently, the monomer solution was continuously fed with a metering pump, simultaneously with line mixing of 160 parts by weight of the aqueous solution of 24 wt % sodium hydroxide, thus preparing the aqueous solution of monomers. Here, a temperature increase by neutralization heat was controlled to 40° C. Further, after continuously line mixing 6 parts by weight of the aqueous solution of 4 wt % sodium persulfate, the solution was continuously fed to a continuous polymerization reactor having a planar polymerization belt at both ends. Thereafter, UV was irradiated for 1 minute, and then thermal polymerization was additionally conducted for 2 minutes to prepare a hydrogel.

(Step 2)

After cutting the hydrogel prepared in step 1 to the average size of about 300 mm or less, reassembled fine powders were additionally introduced into a grinder (equipped with a perforated panel including multiple holes having a diameter of 11 mm) and ground. Here, as the reassembled fine powders, the reassembled fine powders prepared in step 4 below was used, and the introduction rate was 18 wt % based on the hydrogel.

(Step 3)

The hydrogel ground in step 2 was dried in a dryer capable of transferring air volume up and down. Hot air at 180° C. was allowed to flow from the lower side to the upper side for 15 minutes, and to flow from the upper side to the lower side again for 15 minutes, so that the moisture content of the dried powders may become about 2%, thus uniformly drying the hydrogel.

(Step 4)

The polymer dried in step 3 was ground with a grinder and then sieved to obtain a base polymer with a size of 150 to 850 μm. Meanwhile, through the sieving, polymer particles having a particle diameter of less than 150 μm were assembled with water, and used as the reassembled fine powder of step 2.

(Step 5)

100 parts by weight of the base polymer prepared in step 4 was mixed with a crosslinking solution including 3 parts by weight of water, 3 parts by weight of methanol, 0.5 parts by weight of 1,3-propanediol, and 0.1 parts by weight of $Al_2O_3$ particles (BET specific surface area 130 $m^2/g$) as hydrophilic inorganic particles, and then the temperature was raised from room temperature to 180° C. for 25 minutes and maintained at 180° C. for 30 minutes, thus conducting surface crosslinking. The obtained product was cooled and sieved to obtain a surface-crosslinked superabsorbent polymer having a particle diameter of 150 to 850 μm.

(Step 6)

Based on 100 parts by weight of the superabsorbent polymer particles prepared in step 5, as hydrophobic inorganic particles, 0.05 parts by weight of $SiO_2$ particles (BET specific surface area 140 $m^2/g$) of which surface was treated with hexamethyldisilazane was coated using a mixer, thus preparing a superabsorbent polymer.

EXAMPLES 2 TO 8

Each superabsorbent polymer was prepared by the same method as Example 1, except that the hydrophilic inorganic particles, surface crosslinking reaction, and hydrophobic inorganic particles described in the following Table 1 were used.

TABLE 1

| | Inorganic particles mixed in a surface crosslinking solution | | | Surface crosslinking time | | Inorganic particles mixed during post treatment | | |
|---|---|---|---|---|---|---|---|---|
| | Kind of inorganic particles | Surface treatment | content (parts by weight) | Time for temperature rise to 180(minutes) | Time for maintenance above 180(minutes) | Kind of inorganic particles | Surface treatment | content (parts by weight) |
| Example 1 | hyhdrophilic $Al_2O_3$ | Non treated | 0.1 | 25 | 30 | hydrophobic $SiO_2$ | HMDS[1] | 0.05 |
| Example 2 | hyhdrophilic $Al_2O_3$ | Non treated | 0.1 | 15 | 35 | hydrophobic $SiO_2$ | HMDS | 0.05 |
| Example 3 | hyhdrophilic $Al_2O_3$ | Non treated | 0.1 | 35 | 25 | hydrophobic $SiO_2$ | HMDS | 0.05 |
| Example 4 | hyhdrophilic $Al_2O_3$ | Non treated | 0.05 | 25 | 30 | hydrophobic $SiO_2$ | HMDS | 0.03 |
| Example 5 | hyhdrophilic $Al_2O_3$ | Non treated | 0.15 | 25 | 30 | hydrophobic $SiO_2$ | HMDS | 0.08 |
| Example 6 | hyhdrophilic $Al_2O_3$ | Non treated | 0.1 | 25 | 30 | hydrophobic $SiO_2$ | DDS[2] | 0.05 |
| Example 7 | hyhdrophilic $SiO_2$ | Non treated | 0.1 | 25 | 30 | hydrophobic $SiO_2$ | HMDS | 0.05 |
| Example 8 | hyhdrophilic $SiO_2$ | Non treated | 0.1 | 25 | 30 | hydrophobic $SiO_2$ | DDS | 0.05 |

[1]HMDS: Hexamethyldisilazane
[2]DPS: Dimethyldichlorosilane

COMPARATIVE EXAMPLES 1 TO 8

Each superabsorbent polymer was prepared by the same method as Example 1, except that the hydrophilic inorganic particles, surface crosslinking reaction, and hydrophobic inorganic particles described in the following Table 2 were used.

TABLE 2

| | Inorganic particles mixed in a surface crosslinking solution | | | Surface crosslinking time | | Inorganic particles mixed during post treatment | | |
|---|---|---|---|---|---|---|---|---|
| | Kind of inorganic particles | Surface treatment | content (parts by weight) | Time for temperature rise to 180(minutes) | Time for maintenance above 180(minutes) | Kind of inorganic particles | Surface treatment | content (parts by weight) |
| Comparative Example 1 | Hydrophilic $Al_2O_3$ | Non treated | 0.1 | 55 | 20 | Hydrophobic $SiO_2$ | HMDS | 0.05 |
| Comparative Example 2 | Hydrophilic $Al_2O_3$ | Non treated | 0.1 | 15 | 55 | Hydrophobic $SiO_2$ | HMDS | 0.05 |
| Comparative Example 3 | Hydrophilic $Al_2O_3$ | Non treated | 0.1 | 35 | 5 | Hydrophobic $SiO_2$ | HMDS | 0.05 |
| Comparative Example 4 | | (not used) | | 25 | 30 | Hydrophobic $SiO_2$ | HMDS | 0.08 |

TABLE 2-continued

| | Inorganic particles mixed in a surface crosslinking solution | | | Surface crosslinking time | | Inorganic particles mixed during post treatment | | |
|---|---|---|---|---|---|---|---|---|
| | Kind of inorganic particles | Surface treatment | content (parts by weight) | Time for temperature rise to 180(minutes) | Time for maintenance above 180(minutes) | Kind of inorganic particles | Surface treatment | content (parts by weight) |
| Comparative Example 5 | Hydrophilic $Al_2O_3$ | Non treated | 0.15 | 25 | 30 | (not used) | | |
| Comparative Example 6 | Hydrophilic $Al_2O_3$ | Non treated | 0.3 | 25 | 30 | Hydrophobic $SiO_2$ | HMDS | 0.03 |
| Comparative Example 7 | Hydrophilic $Al_2O_3$ | Non treated | 0.05 | 25 | 30 | Hydrophobic $SiO_2$ | HMDS | 0.2 |
| Comparative Example 8 | Hydrophilic $Al_2O_3$ | Non treated | 0.1 | 25 | 30 | Hydrophilic $Al_2O_3$ | Non treated | 0.1 |
| Comparative Example 9 | Hydrophilic $Al_2O_3$ | Non treated | 0.1 | 25 | 30 | Hydrophilic $SiO_2$ | Non treated | 0.1 |
| Comparative Example 10 | Hydrophobic $SiO_2$ | HMDS[1] | 0.1 | 25 | 30 | Hydrophobic $SiO_2$ | HMDS | 0.05 |
| Comparative Example 11 | Hydrophobic $SiO_2$ | DDS[2] | 0.1 | 25 | 30 | Hydrophobic $SiO_2$ | HMDS | 0.05 |

[1]HMDS: Hexamethyldisilazane
[2]DDS: Dimethyldichlorosilane

Experimental Example: Evaluation of the Properties of Superabsorbent Polymer

The properties of the superabsorbent polymers prepared in the examples and comparative examples were evaluated as follows.

(1) Centrifuge Retention Capacity (CRC)

For the superabsorbent polymers of the examples and comparative examples, centrifuge retention capacity (CRC) by absorption rate under no load was measured according to European Disposables and Nonwovens Association (EDANA) standard EDANA WSP 241.3.

Specifically, $W_0$(g, 0.1 g) of the polymers of the examples and comparative examples were uniformly put in an envelope made of non-woven fabrics and sealed, and then soaked in a saline solution of a 0.9 wt % sodium chloride aqueous solution at room temperature. After 30 minutes, the envelope was drained using a centrifuge at 250 G for 3 minutes, and then the weight $W_2$(g) was measured. After the same operation without using a superabsorbent polymer, the weight $W_1$ (g) was measured.

Using each mass obtained, CRC (g/g) was calculated according to the following mathematical formula.

$$CRC(g/g) = \{[W_2(g) - W_1(g) - W_0(g)]/W_0(g)\}$$

(2) Absorbing under Pressure (AUP)

The absorption under pressure (AUP) of 0.7 psi of the superabsorbent polymers of the examples and comparative examples to a saline solution was measured according to the EDANA WSP 242.2 method.

Specifically, on the bottom of a plastic cylinder having an inner diameter of 60 mm, a 400 mesh screen made of stainless was installed. Further, at room temperature and 50% humidity, $W_0$ (g, 0.9 g) of the superabsorbent polymer of which absorption under pressure was to be measured was uniformly sprayed onto the screen. Subsequently, on the superabsorbent polymer, a piston capable of uniformly applying loads of 4.83 kPa (0.7 psi) was put. Here, a piston with an outer diameter of slightly smaller than 60 mm and no gap with the inner wall of the cylinder, and manufactured so as to freely move up and down, was used. The weight $W_1$ (g) of the prepared apparatus was measured.

Subsequently, inside a Petri dish having a diameter of 150 mm, a glass filer with a diameter of 90 mm and a thickness of 5 mm was put, and a 0.9 wt % saline solution was poured into the Petri dish. Here, the saline solution was poured until the surface of the saline solution became horizontal with the upper side of the glass filer. Further, on the glass filter, one piece of a filter paper with a diameter of 90 mm was put.

Subsequently, the above-prepared apparatus was put on the filter paper, and the superabsorbent polymer in the apparatus was allowed to swell by the saline solution under load. After 1 hour, the weight $W_2$ (g) of the apparatus containing the swollen superabsorbent polymer was measured. Using the measured weight, absorption under pressure was calculated according to the following mathematical formula.

$$AUP(g/g) = [W_2(g) - W_1(g)]/W_0(g)$$

(3) Permeability Dependent Absorption Under Pressure (PDAUP)

The permeability dependent absorption under pressure of the superabsorbent polymers of the examples and comparative examples were measured according to EDANA WSP 243.1.

Specifically, on the bottom of a plastic cylinder having an inner diameter of 60 mm, a 400 mesh wire netting made of stainless was installed. At room temperature and 50% humidity, $W_0$ (5.0 g) of the superabsorbent polymer was uniformly sprayed onto the wire netting, and a piston capable of uniformly applying loads of 4.83 kPa (0.7 psi) was put thereon. The piston has an outer diameter of slightly smaller than 60 mm and no gap with the inner wall of the cylinder, and can freely move up and down. The weight $W_1$ (g) of the apparatus was measured. Inside a Petri dish having a diameter of 150 mm, a glass filer with a diameter of 90 mm and a thickness of 5 mm was put, and a 0.9 wt % saline solution was poured into the Petri dish until the surface of the saline solution became the same level as the upper side of the glass filer. On the glass filter, one piece of a filter paper with a diameter of 90 mm was put. The above measuring apparatus was put on the filter paper, and the superabsorbent polymer was allowed to absorb the solution under load for 1 hour. After 1 hour, the measuring apparatus was lifted, and the weight $W_2$ (g) was measured. Permeability dependent absorption under pressure was calculated according to the following Formula 3.

$$PDAUP(g/g) = \{(W_2(g) - W_1(g)\}/W_0(g)$$

(4) Absorption Speed (Vortex Time)

The absorption speed of the superabsorbent polymers of the examples and comparative examples were measured in the unit of seconds, according to the method described in International Patent Publication No. 1987-003208.

Specifically, for the absorption speed (or vortex time), the superabsorbent polymer (2 g) was put in 50 mL of a saline solution at 23° C. to 24° C., the solution was stirred with a magnetic bar (diameter 8 mm, length 30 mm) at 600 rpm, and a time taken until the vortex disappeared was measured in the unit of seconds.

(5) Anticaking Efficiency

The anticaking efficiency of the superabsorbent polymers of the examples and comparative examples were measured.

Specifically, in a glass Petri-dish with a diameter of 95 mm, the superabsorbent polymer (2 g) was uniformly distributed. The petro dish was put in a constant temperature and humidity chamber which is maintained at a temperature of 40° C. and a relative humidity of 80%, left for 10 minutes, and the Petri dish was turned over. After 5 minutes, the weight ($W_1$) of the polymer dropped on the bottom and the weight ($W_2$) of the superabsorbent polymer remaining in the Petri dish were measured, and the anticaking efficiency was calculated according to the following mathematical formula.

Anticaking efficiency (%)=$(W_1)/(W_1+W_2) \times 100$ (6) Dust Number

Using a Dustview II device of Palas, Germany, dust numbers of the superabsorbent polymers (30 g) of the examples and comparative examples were measured.

The measured results are shown in the following Table 3.

TABLE 3

| | CRC (g/g) | AUP (g/g) | PDAUP (g/g) | Vortex (sec) | Dust Number | Anticaking Efficiency (%) |
|---|---|---|---|---|---|---|
| Example 1 | 30.3 | 23.2 | 18.1 | 62 | 0.6 | 83 |
| Example 2 | 26.9 | 22.8 | 18.0 | 64 | 0.5 | 88 |
| Example 3 | 30.1 | 18.5 | 15.3 | 63 | 0.7 | 80 |
| Example 4 | 29.8 | 23.3 | 18.4 | 70 | 0.4 | 39 |
| Example 5 | 30.2 | 21.6 | 16.9 | 60 | 1.8 | 93 |
| Example 6 | 30.2 | 23.3 | 18.1 | 63 | 0.5 | 89 |
| Example 7 | 30.1 | 22.5 | 17.5 | 62 | 0.4 | 84 |
| Example 8 | 30.2 | 22.9 | 17.8 | 63 | 0.4 | 82 |
| Comparative Example 1 | 25.8 | 17.5 | 9.0 | 84 | 2.3 | 25 |
| Comparative Example 2 | 23.5 | 15.5 | 10.3 | 98 | 2.8 | 29 |
| Comparative Example 3 | 33.3 | 13.3 | 5.4 | 81 | 2.1 | 18 |
| Comparative Example 4 | 28.4 | 22.9 | 14.3 | 95 | 2.5 | 28 |
| Comparative Example 5 | 27.9 | 21.5 | 14.9 | 83 | 2.4 | 2 |
| Comparative Example 6 | 28.5 | 13.3 | 8.8 | 75 | 4.8 | 22 |
| Comparative Example 7 | 26.3 | 14.9 | 9.3 | 86 | 10.5 | 83 |
| Comparative Example 8 | 27.7 | 16.4 | 13.5 | 77 | 2.3 | 13 |
| Comparative Example 9 | 27.8 | 16.2 | 13.1 | 75 | 2.2 | 15 |
| Comparative Example 10 | 25.8 | 17.3 | 14.5 | 81 | 3.3 | 65 |
| Comparative Example 11 | 25.5 | 17.8 | 14.7 | 82 | 3.6 | 63 |

The invention claimed is:

1. A superabsorbent polymer comprising:
   a base polymer powder comprising a first crosslinked polymer of water soluble ethylenically unsaturated monomers having acid groups, wherein at least a part of the acid groups are neutralized; and
   a surface crosslink layer formed on the base polymer powder, comprising a second crosslinked polymer obtained by the additional crosslinking of the first crosslinked polymer by a surface crosslinking agent,
   wherein centrifuge retention capacity (CRC) is 26 g/g or more,
   absorption under pressure of 0.7 psi (0.7 AUP) is 18 g/g or more,
   permeability dependent absorption under pressure (PDAUP) is 15 g/g or more,
   absorption speed measured according to a vortex measuring method is 80 seconds or less, and anticaking efficiency is 30% or more,
   wherein the surface crosslink layer comprises hydrophilic inorganic particles, and hydrophobic inorganic particles are included on a surface of the surface crosslink layer.

2. The superabsorbent polymer according to claim 1, wherein a dust number of the superabsorbent polymer is 3 or less.

3. The superabsorbent polymer according to claim 1, wherein the centrifuge retention capacity (CRC) is 28 g/g or more.

4. The superabsorbent polymer according to claim 1, wherein the absorption under pressure of 0.7 psi (0.7 AUP) is 20 g/g or more.

5. The superabsorbent polymer according to claim 1, wherein the permeability dependent absorption under pressure (PDAUP) is 16 g/g or more.

6. The superabsorbent polymer according to claim 1, wherein the absorption speed measured according to a vortex measuring method is 75 seconds or less.

7. The superabsorbent polymer according to claim 1, wherein the anticaking efficiency is measured by the following Mathematical Formula 1:

Anticaking efficiency (%)= $(W_1)/(W_1+W_2) \times 100$  [Mathematical Formula 1]

wherein, in Mathematical Formula 1, $W_1$ is a weight of the superabsorbent polymer dropped on the bottom, after 2 g of the superabsorbent polymer is uniformly sprayed onto a glass Petri dish with an inner diameter of 95 mm, and then moisturized in a constant temperature and humidity chamber of a temperature of 40° C. and relative humidity of 80% for 10 minutes, taken out, and turned over for 5 minutes, and $W_2$ is a weight of the superabsorbent polymer remaining in the glass Petri dish.

8. The superabsorbent polymer according to claim 1, wherein the anticaking efficiency is 40% or more.

9. A method for preparing a superabsorbent polymer comprising:
   conducting crosslinking polymerization of water soluble ethylenically unsaturated monomers having acid groups, wherein at least a part of the acid groups are neutralized, in the presence of an internal crosslinking agent, to form a hydrogel polymer comprising a first crosslinked polymer (step 1);
   coarsely grinding the hydrogel polymer, and drying and grinding to form a base polymer powder (step 2);
   conducting surface crosslinking of the base polymer powder by heat treatment, in the presence of a surface crosslinking solution comprising hydrophilic inorganic particles, to form superabsorbent polymer particles (step 3); and coating hydrophobic inorganic particles on the superabsorbent polymer particles (step 4).

10. The method for preparing a superabsorbent polymer according to claim 9, wherein the hydrophilic inorganic particles are silica particles or metal oxide particles.

11. The method for preparing a superabsorbent polymer according to claim 9, wherein the step 3 comprises surface crosslinking the base polymer powder by raising a temperature to 180° C. for 10 to 50 minutes, and heat treating at a temperature above 180° C. for 10 to 50 minutes.

12. The method for preparing a superabsorbent polymer according to claim 9, wherein the hydrophobic inorganic particles are silica particles or metal oxide particles of which surfaces are treated with a compound having a hydrophobic group.

13. The method for preparing a superabsorbent polymer according to claim 9, wherein the hydrophilic inorganic particles are included in a content of 0.002 to 0.25 parts by weight, based on 100 parts by weight of the base polymer.

14. The method for preparing a superabsorbent polymer according to claim 9, wherein the hydrophobic inorganic particles are included in a content of 0.001 to 0.15 parts by weight, based on 100 parts by weight of the base polymer.

15. The superabsorbent polymer according to claim 2, wherein the hydrophobic inorganic particles are surface-treated with hexamethyldisilazane, polydimethylsiloxane, or dimethyldichlorosilane.

16. The superabsorbent polymer according to claim 1, wherein water soluble ethylenically unsaturated monomers having acid groups is at least one of acrylic acid, methacrylic acid or a monovalent metal salt, a divalent metal salt, an ammonium salt, or an organic amine salt thereof.

17. The superabsorbent polymer according to claim 1, wherein a degree of neutralization is from 40 mol % to 95 mol %.

18. The superabsorbent polymer according to claim 1, wherein centrifuge retention capacity (CRC) is from 26 g/g to 45 g/g, absorption under pressure is from 0.7 psi (0.7 AUP) is 18 g/g to 28 g/g, permeability dependent absorption under pressure (PDAUP) is from 15 g/g to 24 g/g, absorption speed measured according to a vortex measuring method is from 20 seconds to 80 seconds, and anticaking efficiency is from 30% to 98%.

* * * * *